(12) United States Patent
Charlton

(10) Patent No.: US 8,232,045 B2
(45) Date of Patent: Jul. 31, 2012

(54) COLLOIDAL METAL CONJUGATES

(75) Inventor: David E. Charlton, Sunnyvale, CA (US)

(73) Assignee: Inverness Medical Switzerland GmbH, Zug (CH)

( * ) Notice: Subject to any disclaimer, the term of this patent is extended or adjusted under 35 U.S.C. 154(b) by 669 days.

(21) Appl. No.: 11/887,145

(22) PCT Filed: Mar. 28, 2006

(86) PCT No.: PCT/US2006/011323
§ 371 (c)(1),
(2), (4) Date: Aug. 19, 2009

(87) PCT Pub. No.: WO2006/105111
PCT Pub. Date: Oct. 5, 2006

(65) Prior Publication Data
US 2010/0015636 A1    Jan. 21, 2010

Related U.S. Application Data

(60) Provisional application No. 60/665,851, filed on Mar. 29, 2005.

(51) Int. Cl.
*C12Q 1/00* (2006.01)
*G01N 33/553* (2006.01)
(52) U.S. Cl. .............................. 435/4; 436/524; 436/525
(58) Field of Classification Search ........................ None
See application file for complete search history.

(56) References Cited

U.S. PATENT DOCUMENTS

| 4,313,734 A | | 2/1982 | Leuvering |
| 5,120,643 A | * | 6/1992 | Ching et al. ................. 435/7.92 |
| 5,252,496 A | * | 10/1993 | Kang et al. .................... 436/529 |
| 5,714,389 A | | 2/1998 | Charlton et al. |

* cited by examiner

*Primary Examiner* — Chris L Chin
(74) *Attorney, Agent, or Firm* — Steptoe & Johnson LLP

(57) ABSTRACT

Colloidal metal conjugates can be produced in high concentrations suitable for direct use, for example, in immunoassays. The colloidal metal conjugates can be used in devices for qualitative, semi-quantitative, or quantitative determination of the presence of compounds in samples, including biological samples.

19 Claims, 1 Drawing Sheet

COLLOIDAL METAL CONJUGATES

CLAIM OF PRIORITY

This application claims priority under 35 USC 371 to International Application No. PCT/US2006/011323, filed on Mar. 28, 2006, which claims priority to U.S. Provisional Application Ser. No. 60/665,851, filed Mar. 29, 2005, each of which is incorporated by reference in its entirety.

TECHNICAL FIELD

This invention relates to colloidal metal conjugates, devices including a colloidal metal conjugates, and methods of making the colloidal metal conjugates.

BACKGROUND

Colloidal metal conjugates can be used in a variety of applications, including assays, for example, immunoassays. In such applications, the colloidal metal conjugate can be a metal particle bound to an antibody which is capable of binding with a specific antigen. The metal particle can allow the binding to be visualized in an assay by optical or electronic means, including, for example, visual or spectrophotometric observation of color imparted by the size, composition and shape of the metal particle.

SUMMARY

In general, colloidal metal conjugates can be produced in high concentrations suitable for direct use, for example, in immunoassays. The colloidal metal conjugates can be used in devices for qualitative and semi-quantitative determination of the presence of compounds in samples, including biological samples. A method of preparing a colloidal metal conjugate can include forming a composition having a high concentration of metal particles conjugated to an affinity reagent.

The high concentration can advantageously reduce or eliminate the degree of concentration or purification needed to use the colloidal metal conjugate in an immunoassay. This method can quickly and easily produce colloidal metal and colloidal metal conjugates while decreasing the number of processing steps and reducing the amount of the affinity reagent component of the conjugate. Previous methods generally require purification to remove excess affinity reagent from the conjugate.

In one aspect, a method of producing an assay device includes providing a plurality of colloidal metal particles, mixing the plurality of colloidal metal particles with an amount of an affinity reagent substantially equal to the amount that can be conjugated to the colloidal particles to form the conjugate, and depositing the conjugate directly on or within a substrate.

In another aspect, a method of producing a metal conjugate includes providing a plurality of colloidal metal particles and mixing the plurality of colloidal metal particles with an amount of an affinity reagent substantially equal to the amount that can be conjugated to the colloidal particles to form the conjugate.

In another aspect, a composition includes a plurality colloidal metal particles having a maximum optical density of greater than 2, each of the plurality of colloidal metal particles conjugated to an affinity reagent. The composition is substantially free of aggregated metal particles and substantially free of unbound affinity reagent. The plurality of colloidal metal particles can have a maximum optical density of between 3 and 7.5.

In another aspect, an assay device includes an assay strip including a composition including a colloidal metal conjugate, the colloidal metal conjugate including a metal particle conjugated to an affinity reagent. The composition is substantially free of aggregated metal particles and substantially free of unbound affinity reagent.

In embodiments, the composition and methods can include one or more of the following variations.

The conjugate can be deposited directly on or within a substrate by placing the conjugate on a surface of the substrate or within the substrate without purifying the conjugate, or without concentrating the conjugate, or both.

The plurality of colloidal metal particles can have a maximum optical density of at least 2, less than 8, between 3 and 7.5, or between 4 and 7.

The affinity reagent can include a biomolecule, such as an antibody, which can be a mixture of an antigen-specific antibody and a non-specific antibody. The metal can be gold.

A metal conjugate can be obtained by the methods described above. An assay device can include the metal conjugate obtained by the methods.

The details of one or more embodiments are set forth in the drawings and description below. Other features, objects, and advantages will be apparent from the description, the drawings, and from the claims.

DETAILED DESCRIPTION

Figure 1:
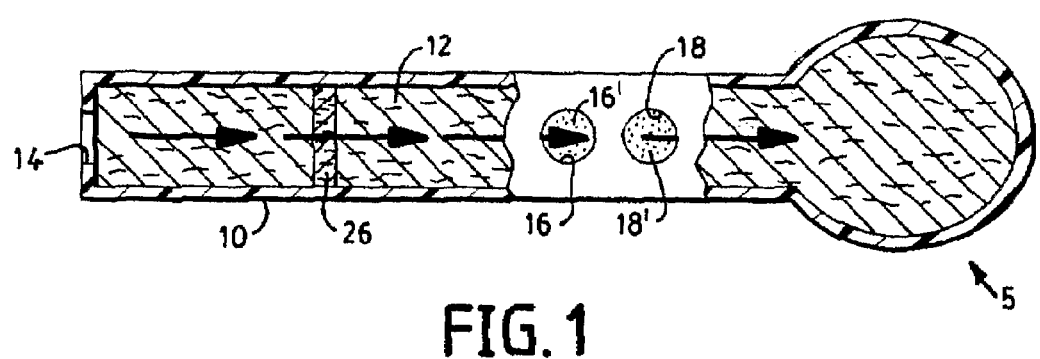
FIG. 1 is diagram illustrating a top cross-sectional view of a diagnostic device.

A colloidal metal solution and colloidal metal conjugate can be prepared in a manner that reduces or eliminates the purification or concentration of the product. The resulting colloidal metal composition can be used directly in a device or assay. A method of preparing a colloidal metal conjugate includes forming a composition having a high concentration of metal particles conjugated to an affinity reagent.

The metal particles can have a diameter of between 5 and 100 nm. The metal can be a metal or transition metal, a metal or transition metal compound, or polymer nuclei coated with a metal or transition metal or a metal or transition metal compound, or an alloy thereof. For example, the metal can be gold, platinum, silver, iron, copper, selenium, chromium, vanadium, titanium, or manganese, or an alloy thereof. The metal compound or transition metal compound can be a metal salt, sulfide, oxide, hydroxide or similar compound. In particular, the metal particle can be a gold particle.

The affinity reagent can include a biomolecule, for example, a nucleotide, a nucleotide sequence, a peptide, a protein, an antibody, an antibody fragment, an antigen, streptavidin, biotin, receptor fragment, or other reactive molecule. The antibody can include antigen-specific antibody, a non-specific antibody or a mixture thereof. The antibody can be, for example, an antibody capable of selectively binding a hapten, such as a drug, a biomolecule, steroid, medicinal drug, or another affinity reagent. The binding can be selective. The drug can be tetrahydrocannabinol, an amphetamine or group of amphetamines, a barbiturate or group of barbiturates, a benzodiazepine or group of benzodiazepines, cocaine, ecstasy, methadone, methamphetamine, morphine, or phencyclidine, or a metabolite thereof.

The high concentration of colloidal metal particles or high concentration of colloidal metal conjugate can be determined by measuring the optical density (or absorbance/reflectance) of a solution or suspension of the colloid at a particular wavelength. The maximum optical density of a solution or suspension is the highest absorbance or reflectance of the solution within a wavelength range of, for example from 250 nm to 850 nm. The maximum optical density can be determined by scanning the wavelength range, for example with a UV/VIS spectrophotometer, to identify the wavelength at which the maximum optical density occurs. For colloidal gold particles, the maximum optical density occurs between 520 and 560 nm, and can be measured at 540 nm. The high concentration of colloidal metal particles can have a maximum optical density of at least 2, at least 3, less than 8, between 3 and 7.5, between 4 and 7, or between 5 and 7. Concentrations that tend to agglomerate are not desirable for creating stable and useful sources of colloidal metal particles.

A colloidal metal conjugate solution having a high concentration of conjugated particles, such as, for example, a metal particle bound to an affinity reagent can be prepared directly from a high concentration of colloidal metal particles. In general, the high concentration of colloidal metal conjugates does not need to be significantly purified or concentrated. By avoiding purification or concentration, time consuming processes such as centrifugation, washing, and agitation to resuspend the particles can be avoided, or minimized in the process of making the conjugate. This significantly reduces material losses, particle aggregation, and time losses during preparation. Preparation of high concentrations of particles can be accomplished in 30 minutes or less. When using other methods of preparing colloidal metal particles prior to this discovery, concentration and purification steps can require an hour or longer to complete, since the methods typically produce low concentrations of particles, having maximum optical densities in the range of 0.5 to 1.5, thereby necessitating the concentrating and washing process.

Generally, the process of directly preparing a high concentration of colloidal metal conjugate solution includes adding an amount of affinity reagent substantially equal to the amount that can be conjugated to the colloidal particles, which can be considered the maximum loading value of the colloidal particles. The maximum loading value for a colloidal metal particle composition can be determined theoretically, for example, by calculating the surface area of the particles and number of particles present, or experimentally, for example, through adsorption experiments, thereby allowing the conjugate to be prepared without using an excessive amount of the affinity reagent.

For example, the amount of affinity reagent to be added to colloidal metal particles can be determined by testing varying concentrations of antigen-specific antibody and non-specific antibody. Non-specific antibody may be, for example, IgG antibodies from a mouse, goat, and rabbit. For example, the total antibody solution can be in the range of between 0.01 and 0.20 mg per 20 mL gold colloid solution, for example, 0.0 mg per 20 mL gold colloid solution having an optical density of between 3 to 7 at 540 nm. In other circumstances, the total antibody solution can be in the range of between 0.01 and 0.05 mg per 20 mL gold colloid solution having an optical density in the range of between 4.5-6.5 at 540 nm. In examples, total amounts of antibody and gold solution can be used so long as the concentration is maintained at the equivalent of 0.001 to 0.10 mg total antibody per 20 mL gold colloid solution or 0.1 to 10 mg total antibody per 20 mL gold colloid solution. Generally, the amount of antibody can be designed to completely, or almost completely, bind to gold particles. The resulting mixture can be cleaner than a mixture prepared by old methods with fewer, or substantially no unbound antibody molecules.

The methodology for producing an optimized gold colloid solution may be applied to numerous applications. In one example, the optimized gold colloid solution can be used in immunoassays. For example, in one embodiment, gold colloid solution is mixed with an antibody solution of anti-THC antibody and mouse IgG antibody. The labeled anti-THC antibody and mouse IgG are then used in a competitive assay for detecting the presence of tetrahydrocannabinol (THC) metabolite.

For biological assays, such as immunoassays, a sufficiently high OD range for making a device involves using a colloidal metal conjugate is between 0.5 and 7.0 OD as measured at its maximum. The optical density can be measured at other wavelengths, but typically is measured within the visible spectrum, for example, between 375 nm and 740 nm. For example, a colloidal metal conjugate can be prepared without a purifying step or a concentrating step, or both, and having a maximum optical density between 3 and 7 by mixing a high concentration of colloidal metal particles (e.g., 0.1 to 5 mg/mL) having an optical density between 3 and 7 with an amount of antibody of between, for example, 0.01 and 10 mg/mL of gold colloid solution. This conjugate can then be used directly, or can be diluted for use in an assay.

The total amount of antibody used is defined within a range, the ratio of antigen-specific antibody and non-specific antibody can be determined based on a dose curve. For example, in a competitive assay for THC, the assay can be designed to detect doses of 50 ng THC/mL urine and higher. A competitive assay can rely on competition for binding to a specific antibody between THC present in the sample and THC linked to an enzyme. The enzyme can be chosen such that enzyme activity results in color formation. In the absence of free THC in the sample, the specific antibody binds to the enzyme-linked THC, which causes a decrease in enzyme activity; in other words, the less THC present, the less color that develops.

Illustrative examples of preparing colloidal metal conjugates follow.

A 1% sodium citrate solution was prepared by adding 10.0 g sodium citrate (Sigma) to a 1 L volume of deionized water. The mixture was stirred for approximately 5 to 10 minutes until the sodium citrate was completely dissolved. The sodium citrate solution was stored at ambient room temperature.

A 2% gold chloride solution was prepared by adding 20.0 g gold chloride (Sigma-Aldrich, gold (III) chloride trihydrate) to a 1 L volume of deionized water. The mixture was stirred for approximately 5 to 10 minutes until the gold chloride was completely dissolved. The gold chloride solution was stored at ambient room temperature in a light shielded container.

A colloidal gold solution was prepared as follows. A 240.0 mL aliquot of the 1% sodium citrate solution (as prepared above) was placed into a container. A 40.0 mL aliquot of the 2% gold chloride solution (as prepared above) was placed into a separate container. container holding 1 L of deionized water and a magnetic stir bar was placed on a heating mantel. The heating mantel was turned on to full power. The previously measured volume of 240.0 mL 1% sodium citrate solution was added to the container. A temperature probe was placed into the solution. The solution was heated until it reached 98° C., at which time the previously measured volume of 40 mL 2% gold chloride solution was added to the container. The mixture was quickly mixed and allowed to come to a boil. Then the heat was turned off and permitted to boil for 3 to 5 minutes. The solution was then removed from the heat, covered, and allowed to cool to room temperature. The container was then stored at ambient temperature in the dark. The colloidal gold solution had an optical density of 4.98 at 540 nm.

An anti-THC colloidal gold conjugate was prepared as follows. An antibody solution was prepared by adding 0.03 mg/mL Anti-THC mAb (Biostream, PN: ND-TA2201, LN: TA-03H02) and 0.02 mg/mL Mouse IgG (Biostream, Biostride, Biocapture, Omega, Biospecific, and YJ Bioproducts) to 1.0 mL of deionized water. The solution was mixed by vortexing. Next, the entire volume of the antibody solution (as prepared above), 2 mL of 30% BSA, 2 mL 1 M HEPES buffer, 2 mL 50% concentrated sucrose solution, and 2 mL 10% Triton X-100 solution were placed into separate containers. A 20 mL aliquot of the gold colloid solution (O.D. 4.98 at 540 nm) was placed in a beaker containing a stirbar. 0.8 mL 1 M HEPES buffer was added to the beaker. The beaker was placed on a stirplate. The mixture was stirred vigorously at a setting of 250 rpm. As soon as the stirplate reached 250 rpm, each of the previously measured solutions of the antibody, BSA, HEPES buffer, 50% concentrated sucrose and 10% Triton X-100 were added to the beaker within a two minute period to form the colloidal gold conjugate. The colloidal gold conjugate was transferred to a light protected storing container. The colloidal gold conjugate was stable at 2-8° C. for up to 1 month.

Figure 2:
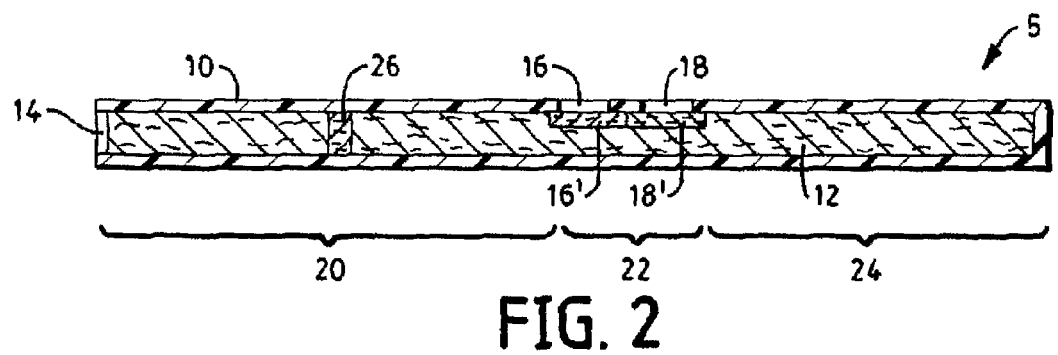
FIG. 2 is diagram illustrating a side cross-sectional view of a diagnostic device.

The colloidal gold conjugate was suitable for use in an assay device directly or upon dilution. Suitable assays and devices therefore, may be homogeneous or heterogeneous. An example of a heterogeneous assay device is one referred to in the art as having a lateral flow porous carrier such as disclosed by U.S. Pat. No. 5,602,040, which is incorporated by reference in its entirety. The porous carrier can be nitrocellulose. Alternatively, the assay device may be constructed from a non-porous lateral flow type assay device such as disclosed by U.S. Pat. No. 6,143,576. The assay device may be incorporated within a housing. One such embodiment is described as follows. Referring to FIGS. 1 and 2 show test cell 5 including an outer, molded casing 10 which defines a hollow, elongate enclosure filled with a porous carrier 12. Casing 10 also defines a test liquid inlet 14 and a pair of openings 16, 18 comprising windows through which porous carrier 12 is visible.

Porous carrier 12 and the interior of casing 10 together define a flow path passing generally from left to right in FIGS. 1 and 2. When the test cell is placed with inlet 14 disposed within or otherwise in contact with a liquid sample, the liquid is transported by capillary action, wicking, or simple wetting along the flow path through downstream flow section 20, test volume 22, and into reservoir volume 24, generally as depicted by the arrows. The flow section 20 of the flow path disposed inwardly of the inlet 14 serves as a filter which can remove particulate matter and interfering factors from test samples. Filtration means 20 downstream of the inlet 14 can help prevent false positive test results.

Disposed within porous carrier 12 is a band 26 of dehydrated conjugate, e.g., an antibody-colloidal metal conjugate. As the liquid sample moves past band 26, the conjugate is entrained in the liquid, reconstituted, and reacts or competes with ligand, if present, dissolved in the liquid sample. Alternatively, conjugate band 26 may be eliminated, and the conjugate added to the test liquid prior to its introduction to test cell 5.

Within the volume of porous carrier 12 disposed directly beneath circular openings 16 and 18 in casing 10 is disposed, respectively, control site 16' and test site 18'. In the drawing, the control and test site are illustrated as being disposed serially along the flow path. Alternatively, the control and test site or sites may be disposed side by side or in another spatial relationship.

Test site 18' includes a preselected quantity of antibody against an epitope of the ligand to be detected immobilized in the flow path. Control site 16' is preferably identical in size and chemical makeup to test site 18', excepting that the immobilized antibody present at the test site 18' is omitted at the control site 16'. Thus, any nonspecific aggregation of, e.g., ligand-conjugate or free conjugate, which occurs at test site 18' also will occur at control site 16'. A deeper color at test site 18' as compared with control site 16' can be a positive indication of ligand in the sample in a sandwich assay. Control site 16' may be eliminated if a reduction in sensitivity can be tolerated.

Generally, antibody or other binding protein may be immobilized at test site 18' using adsorption, absorption, or ionic or covalent coupling, in accordance with known methods. For example, a monoclonal antibody against an epitope of the ligand can be immobilized on latex beads, which are then to entrapped or otherwise linked in porous carrier 12 at region 18'. Control site 16' can be fabricated identically, except that the latex beads contain non-specific immunoglobulin, e.g., immunoglobulin from bleedings from an animal that has not been immunized.

Disposed beyond test volume 22 is a reservoir volume 24 comprising a relatively large mass of sorbent or supersorbent material. The purpose of reservoir volume 24 is to assure that a reasonably large amount of test liquid is drawn through test volume 22. Increasing the volume of reservoir 24 can have the effect of increasing the sensitivity of the assay procedure, as it results in an increase in the amount of ligand passing through the test area 22. Suitable sorbents include commercial materials of the type available, for example, from The Dow Chemical Company of Midland, Mich., and the Chemical division of American Colloid, Arlington Heights, Ill. These materials can absorb many times their weight in water and are commonly used in disposable diapers. They comprise lightly crosslinked polyacrylate salts, typically alkali metal salts.

A fluid, for example, a biological fluid, including, for example, blood, blood plasma, serum, interstitial fluid, saliva, sweat, urine, semen, tear, amniotic fluid, an extracted sample such as throat, vaginal or nasal swab, a tissue homogenate or a tissue effluent can be assayed by the device.

Surprisingly, the method results in a colloidal metal conjugate solution which can be produced relatively quickly in comparison to previous methods. The metal conjugate solution produced according to the method significantly reduces processing time because there is no need for, or a substantially reduced need for, purification or concentration steps. The colloidal metal conjugate can be used directly in an assay device.

Other embodiments are within the scope of the following claims.

What is claimed is:
1. A method of producing an assay device comprising:
providing a plurality of colloidal metal particles;
mixing the plurality of colloidal metal particles with an amount of an affinity reagent substantially equal to the amount that can be conjugated to the colloidal particles to form the conjugate; and depositing the conjugate directly on a substrate, wherein depositing the conjugate directly on a substrate includes placing the conjugate on a surface of the substrate without purifying the conjugate.

2. The method of claim 1, wherein depositing the conjugate directly on a substrate includes placing the conjugate on a surface of the substrate without concentrating the conjugate.

3. The method of claim 1, wherein the plurality of colloidal metal particles has a maximum optical density of at least 2.

4. The method of claim 3, wherein the plurality of colloidal metal particles has a maximum optical density of less than 8.

5. The method of claim 1, wherein the plurality of colloidal metal particles has a maximum optical density of between 3 and 7.5.

6. The method of claim 1, wherein the affinity reagent is a biomolecule.

7. The method of claim 1, wherein the affinity reagent is an antibody.

8. The method of claim 1, wherein the affinity reagent is a mixture of an antigen-specific antibody and a non-specific antibody.

9. The method of claim 1, wherein the metal is gold, platinum, silver, iron, copper, selenium, chromium, vanadium, titanium, or manganese, or an alloy thereof.

10. The method of claim 1, wherein the metal is gold.

11. A method of producing an assay device comprising:
providing a plurality of colloidal metal particles;
mixing the plurality of colloidal metal particles with an amount of an affinity reagent substantially equal to the amount that can be conjugated to the colloidal particles to form the conjugate; and
depositing the conjugate directly on a substrate, wherein the affinity reagent is a mixture of an antigen-specific antibody and a non-specific antibody.

12. The method of claim 11, wherein depositing the conjugate directly on a substrate includes placing the conjugate on a surface of the substrate without concentrating the conjugate.

13. The method of claim 11, wherein the plurality of colloidal metal particles has a maximum optical density of at least 2.

14. The method of claim 13, wherein the plurality of colloidal metal particles has a maximum optical density of less than 8.

15. The method of claim 11, wherein the plurality of colloidal metal particles has a maximum optical density of between 3 and 7.5.

16. The method of claim 11, wherein the affinity reagent is a biomolecule.

17. The method of claim 11, wherein the affinity reagent is an antibody.

18. The method of claim 11, wherein the metal is gold, platinum, silver, iron, copper, selenium, chromium, vanadium, titanium, or manganese, or an alloy thereof.

19. The method of claim 11, wherein the metal is gold.

* * * * *